Figure 1:
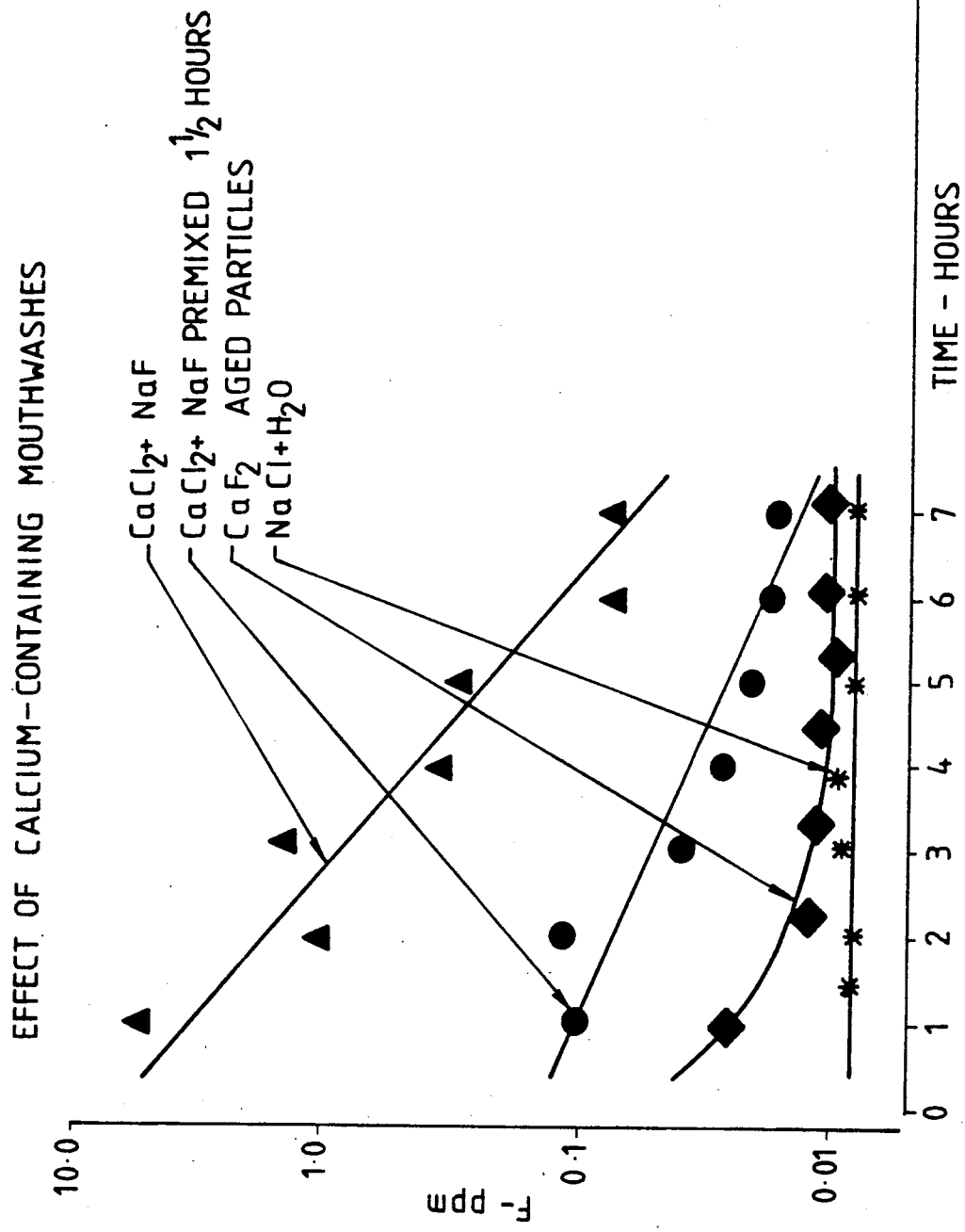

United States Patent [19]

Clarkson et al.

[11] Patent Number: 5,045,305

[45] Date of Patent: Sep. 3, 1991

[54] ORAL HYGIENE COMPOSITION

[75] Inventors: John R. Clarkson, Wirral; Ralph M. Duckworth, Nr Chester; Andrew M. Murray, Cheshire; Timothy J. Price, Chester, all of England

[73] Assignee: Chesebrough-Pond's USA Co., Division of Conopco, Inc., Greenwich, Conn.

[21] Appl. No.: 449,489

[22] Filed: Dec. 11, 1989

Related U.S. Application Data

[63] Continuation of Ser. No. 7/267,582, Nov. 7, 1988, abandoned, which is a continuation of Ser. No. 7/102,213, Sep. 29, 1987, abandoned.

[30] Foreign Application Priority Data

Oct. 2, 1986 [GB] United Kingdom ............... 8623643

[51] Int. Cl.$^5$ ............................ A61K 7/18; A61K 7/16
[52] U.S. Cl. ........................................ 424/52; 424/49; 514/835
[58] Field of Search ...................... 424/49, 52; 514/835

[56] References Cited

U.S. PATENT DOCUMENTS

| | | | |
|---|---|---|---|
| 3,711,604 | 1/1973 | Colodney | 424/52 |
| 4,080,440 | 3/1978 | DiGiulio et al. | 424/52 |
| 4,083,955 | 4/1978 | Grabenstetter | 424/52 |
| 4,098,435 | 7/1978 | Weyn | 424/52 |
| 4,108,980 | 8/1978 | Duff | 424/52 |
| 4,211,341 | 7/1980 | Weyn | 222/94 |
| 4,714,608 | 12/1987 | Rölla | 424/52 |
| 4,837,007 | 6/1989 | Duckworth | 424/52 |

FOREIGN PATENT DOCUMENTS

| | | |
|---|---|---|
| 40738 | 12/1981 | European Pat. Off. . |
| 89136 | 9/1983 | European Pat. Off. . |
| 8602265 | 4/1986 | European Pat. Off. . |
| 777556 | 6/1957 | United Kingdom . |
| 1090340 | 11/1967 | United Kingdom . |
| 1408922 | 2/1973 | United Kingdom . |
| 1452125 | 10/1976 | United Kingdom . |
| 2174301 | 11/1986 | United Kingdom . |

Primary Examiner—Ronald W. Griffin
Attorney, Agent, or Firm—Milton L. Honig

[57] ABSTRACT

An oral hygiene product especially for inhibiting caries is the form of toothpaste or mouthwash. The product maintains a low fluoride ion concentration in the mouth for longer periods than conventional products by the rapid precipitation of calcium fluoride either in the mouth or immediately prior to use. The product comprises a composition containing calcium ions and a further composition containing fluoride ions. The ion product of the calcium and fluoride ions of the combined product preferably exceeds $3 \times 10^{-8}$ mol$^3$ dm$^{-9}$.

6 Claims, 2 Drawing Sheets

ORAL HYGIENE COMPOSITION

This application is a continuation of Ser. No. 07/267,582, filed Nov. 11, 1988, now abandoned, which is a continuation of Ser. No. 07/102,213, filed Sep. 29, 1987, now abandoned.

This invention relates to oral products, more particularly oral hygiene products which are effective to combat dental caries.

It is well known to include water-soluble fluorine-containing salts, for example sodium fluoride or sodium monofluorophosphate, in oral products, especially mouthwashes and toothpastes, and that by regular use of such products the incidence of dental caries can be reduced. It is believed that the fluoride ion or monofluorophosphate ion, interacts with the tooth substance to increase its resistance to acid attack and to aid repair of carious enamel. However, the opportunity for this efficacious interaction to occur is short-lived because the oral fluoride level falls off rapidly after use of a mouthwash or toothpaste.

There have been attempts in the past to provide means for maintaining a certain concentration of fluoride ions in the mouth over a longer period. These have included proposals for locating a fluoride ion source in the mouth, for example as part of an orthodontic appliance.

The Applicants have investigated the possibility of depositing particles of a fluoride ion-releasing material in the mouth and have discovered that surprising results are achieved through the use of particles of freshly precipitated calcium fluoride, as is more particularly described hereinafter.

It is already known to treat teeth to provide anticaries protection with compositions containing calcium ions and fluoride ions. Such compositions are described in EP-A-89 136 (Procter & Gamble) and they comprise a calcium ion source, a fluoride ion source and a calcium sequestering agent possessing specific solubility and binding properties to control the precipitation of calcium fluoride. The calcium-sequestering agent present in these compositions has a stability constant sufficient to inhibit uncontrolled and rapid precipitation of calcium fluoride.

In U.S. application Ser. No. 4,080,440 (DiGuilo et al) there is described a two-part product for example mouthwash or toothpaste, for remineralising demineralised tooth enamel, consisting of a first solution containing calcium ions and a second solution containing phosphate ions and optionally fluoride ions, which solutions when mixed together form a metastable solution having a pH of about 4 or below. The metastable solution is applied to the tooth surface within 5 minutes of its formation. The ions diffuse into the demineralised subsurface where due to a rise in pH calcium phosphate and calcium fluoride are precipitated.

GB-A-1 452 125 (Procter & Gamble) also describes a two-part oral treatment product comprising a first solution containing calcium ions and a second solution containing phosphate ions and fluoride ions, the solutions being applied to the tooth surface sequentially. The respective ions diffuse to the subsurface dental enamel, the ions of the second applied solution coming into contact with those previously deposited and forming a precipitate which is bound to the tooth structure.

There have also been described in the literature various compositions containing both a calcium compound and a fluoride compound and wherein means are provided to inhibit the formation of calcium fluoride; examples are EP-A-40 738 (Richardson-Vicks), GB-A-777 556 (Colgate-Palmolive) and U.S. application Ser. No. 4,098,435 (Weyn).

GB 1 090 340 (Warner Lambert) discloses a one-part oral composition containing calcium and fluoride ions. Any calcium fluoride in such compositions will not be freshly precipitated.

GB 1 408 922 (Blendax) and U.S. Pat. No. 4 108 980 (Colgate) disclose compositions comprising calcium, phosphate and fluoride ions for remineralising dental enamel. The disclosed compositions contain such high levels of phosphate that preferential precipitation of solid calcium phosphate phases such as octacalcium phosphate and hydroxyapatite would deplete the liquid phase composition of calcium ions rather than allow calcium fluoride precipitation. Further, any calcium fluoride precipitation would occur slowly due to the presence of large amounts of the crystal growth inhibitor, phosphate.

The present invention provides an oral preparation for inhibiting caries, which comprises as a combined preparation a first composition and a second composition for admixing in the mouth or for admixing immediately prior to introduction into the mouth, wherein the first composition comprises an aqueous solution containing calcium ions, the second composition comprises an aqueous solution containing fluoride ions, the first and second compositions being such that when mixed rapid precipitation of calcium fluoride occurs.

For optimum retention of fluoride in the mouth the ratio of calcium ions to fluoride ions should be stoichiometric (i.e. 1:2).

Rapid precipitation of calcium fluoride is induced by using high concentrations of calcium ions and fluoride ions. Thus, the initial ion product (IP) on mixing the two compositions which is given by the equation:

$$IP = (Ca^{2+})(F^-)^2$$

where $(Ca^{2+})$ = calcium ion concentration, and
$(F^-)$ = fluoride ion concentration should exceed the solubility product of calcium fluoride, $2.85 \times 10^{-11}$ mol$^3$ dm$^{-9}$ at 25° C., by at least 1000 times. More preferably, the above ion product should exceed $3 \times 10^{-7}$ mol$^3$ dm$^{-9}$.

Rapid precipitation of calcium fluoride is not favoured by low concentrations of calcium ions and fluoride ions. At low concentrations of the aforementioned ions a metastable solution may be formed so that precipitation proceeds slowly for many minutes after the ions are mixed. Rapid precipitation is also inhibited by crystal growth inhibitors such as hydrogen phosphate ions ($HPO_4^{2-}$).

The presence of substances which react with either calcium ions or fluoride ions to produce material having a solubility less than that of calcium fluoride are not advantageous. The presence of substances which reduce the amount of free calcium or fluoride ions before the compositions are mixed are also not advantageous. Examples of such materials are metal ion sequestrants such as EDTA, which react with calcium ions to form complexes, and alumina abrasive particles which bind fluoride.

In preferred embodiments of the invention the composition is in the form of a two-part toothpaste or a two-part mouthwash.

Calcium chloride is used in a preferred embodiment of the invention. Preferably a calcium ion concentration of at least 3.95 mM is used, more preferably at least 8 mM. Calcium ion levels in excess of 0.3 M provide no additional benefit and would generally not be used.

Sodium fluoride is used in a preferred embodiment of the invention. A fluoride ion concentration of at least 7.9 mM is preferably used, more preferably at least 16 mM. Fluoride ions are preferably less than 0.3 M.

One or both of the compositions may contain adjuvants. Such adjuvants may include colouring agents, flavours, humectants, abrasives, detergents, preferably nonionic detergents, and the like and other therapeutic agents compatible with calcium or fluoride ions.

In use the first and second compositions are admixed in the mouth or immediately prior to introduction into the mouth. A delivery system providing for physical separation of the two compositions and for simultaneous or sequential delivery of the compositions may also be used.

The efficacy of the freshly precipitated calcium fluoride in maintaining fluoride ion levels in the mouth is demonstrated by the following experiments.

EXPERIMENT 1

Procedure

The procedure employed for each test was as follows:

(i) a 2ml mouthwash was held in the mouth for one minute and then expectorated. Such mouthwashes consisted of two 1 ml solutions, which were either applied separately or mixed before application.

(ii) saliva samples were collected at regular intervals for several hours after mouthwash application.

(iii) Saliva samples were buffered to pH 5 by adding 10% by weight of TISAB buffer and then fluoride activities were measured using a fluoride ion specific electrode (Orion 94-O9).

The following aqueous solutions were used:

(a) 0.0526 M sodium chloride (b) 0.0526 M calcium chloride and 0.1053 M sodium fluoride mixed immediately prior to application (c) as (b) but mixed 1.5 hours before application.

(d) a suspension of the equivalent concentration of calcium fluoride to that of (c) diluted from a concentrated stock prepared 3 months before application. (Aged calcium fluoride).

Results

FIG. 1 shows that salivary fluoride levels resulting from application of mouthwashes containing freshly precipitated calcium fluoride are significantly higher than the corresponding values for aged precipitates. The mouthwash containing the most aged calcium fluoride particles (three months old) gave salivary fluoride values only slightly greater than the 'baseline' values measured after application of sodium chloride solution.

EXPERIMENT 2

The following experiment was performed to demonstrate that a mouthwash containing freshly precipitated calcium fluoride is capable of maintaining fluoride in the mouth at a higher level than a sodium fluoride mouthwash of the same fluoride content.

Procedure

The experiment was carried out in a similar manner to that described above using the following aqueous solutions;

(i) 0.0526 M calcium chloride and 0.1052 M sodium fluoride mixed immediately prior to application (ii) 0.0526 M sodium fluoride.

Results

Figure 2:
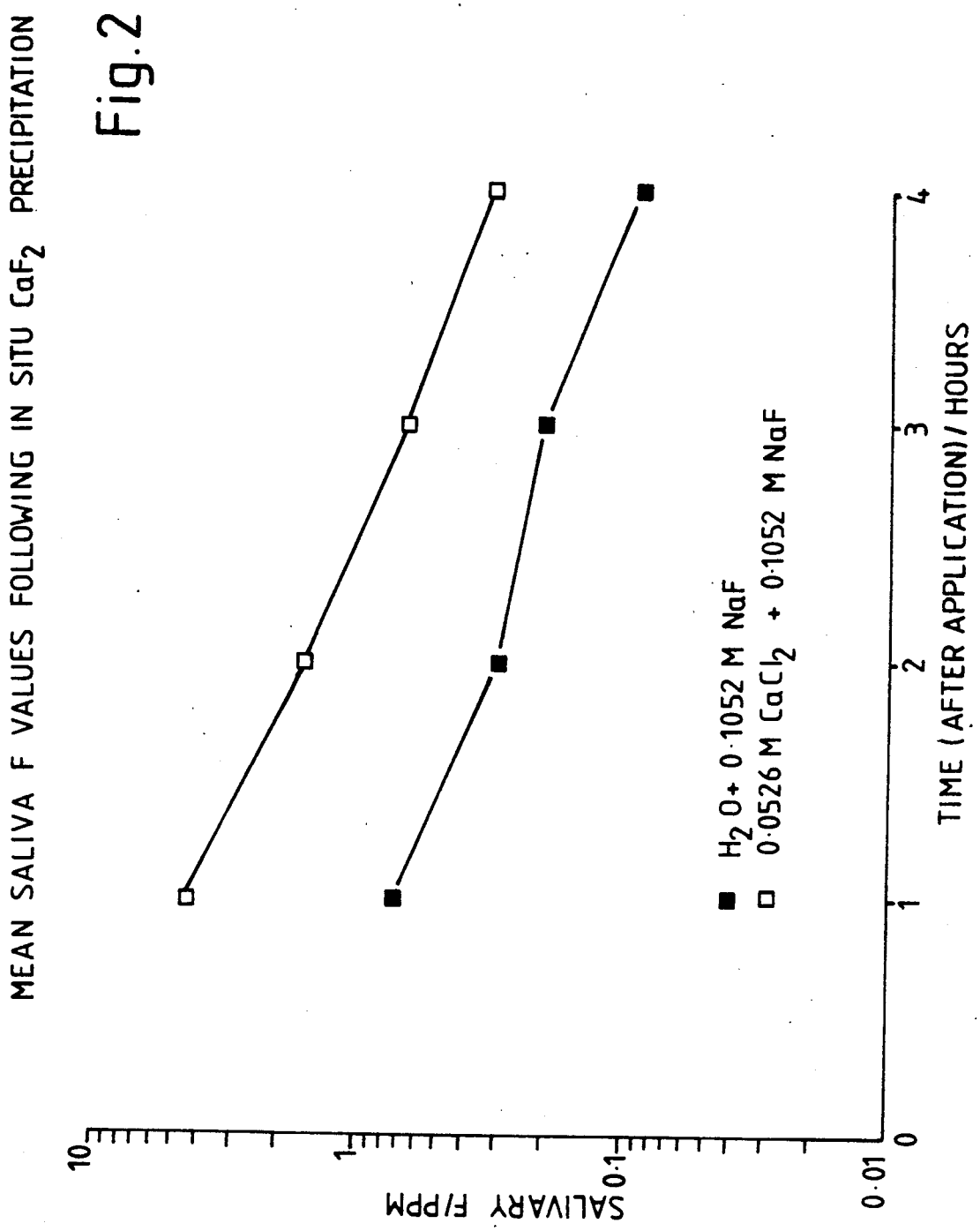

FIG. 2 shows that salivary fluoride levels resulting from the application of mouthwashes containing freshly precipitated calcium fluoride are significantly higher than the corresponding values for sodium fluoride.

The invention is illustrated by reference to the following examples. All percentages are by weight.

EXAMPLE 1

| Mouthwash | % |
|---|---|
| First composition | |
| Sodium fluoride | 0.11 |
| Sorbitol syrup (70% solution) | 15.0 |
| Ethanol | 10.0 |
| Nonionic detergent | 0.4 |
| Saccharin | 0.04 |
| Flavour | 0.15 |
| Water to | 100 |
| Second composition | |
| Calcium chloride dihydrate | 0.195 |
| Sorbitol syrup (70% solution) | 15.0 |
| Ethanol | 10.0 |
| Nonionic detergent | 0.4 |
| Saccharin | 0.04 |
| Flavour | 0.15 |
| Water to | 100 |

Approximately 5 ml of each component are mixed together immediately before use.

EXAMPLE 2

| Toothpaste | % |
|---|---|
| First composition | |
| Sodium fluoride | 0.44 |
| Abrasive silica | 14.0 |
| Thickening silica | 8.0 |
| Sorbitol syrup (70% solution) | 50.0 |
| Sodium carboxymethylcellulose | 0.65 |
| Nonionic detergent | 1.5 |
| Flavour | 1.0 |
| Saccharin | 0.1 |
| Titanium dioxide | 1.0 |
| Water to | 100 |
| adjust pH to 7.0-7.5 with NaOH. | |
| Second composition | |
| Calcium chloride dihydrate | 0.78 |
| Abrasive silica | 14.0 |
| Thickening silica | 8.0 |
| Sorbitol syrup (70% solution) | 50.0 |
| SCMC | 0.65 |
| Nonionic detergent | 1.5 |
| Flavour | 1.0 |
| Saccharin | 0.1 |
| Titanium dioxide | 1.0 |
| Water to | 100 |
| adjust pH to 7.0-7.5 with NaOH. | | to be mixed in equal proportions in use.

Toothpaste-mouthwash combinations are also within the scope of the invention. One such combination can be achieved by applying the first composition, 1 ml of a mouthwash of composition

|  | % |
| --- | --- |
| Sodium fluoride | 0.44 |
| Sorbitol syrup (70% solution) | 15.0 |
| Ethanol | 10.0 |
| Nonionic detergent | 0.4 |
| Saccharin | 0.04 |
| Flavour | 0.15 |
| Water to | 100.0 | and then immediately brushing with the second composition of Example 2.

The oral product of the invention may also be incorporated in other oral preparations or formulations such as dual composition lozenges, sweets and chewing gum.

We claim:

1. A method of inhibiting dental caries which comprises the steps of:

admixing a first composition containing a source of calcium ions from calcium chloride and a second composition containing a source of fluoride ions from sodium fluoride thereby forming an oral preparation of calcium fluoride; and introducing said oral preparation into a mouth, said admixing step occurring outside the dentulous mouth but less than 1.5 hours prior to said introduction into the mouth.

2. The method as claimed in claim 1 wherein the ion product (IP) of the calcium ions and fluoride ions as hereinbefore defined exceeds $3 \times 10^{-8}$ mol$^3$ dm$^{-9}$ on mixing.

3. The method as claimed in claim 1 wherein the calcium salt is calcium chloride.

4. The method as claimed in claim 1 wherein the fluoride salt is sodium fluoride.

5. The method as claimed in claim 1 wherein the compositions are in the form of a two-part mouthwash.

6. The method as claimed in claim 1 wherein the compositions are in the form of a two-part toothpaste.

* * * * *